United States Patent [19]

Fabian et al.

[11] Patent Number: 5,315,685
[45] Date of Patent: May 24, 1994

[54] COMPONENT FOR THE TRANSMISSION OF HIGH-ENERGY LIGHT, AND THE APPLICATION OF THE COMPONENT

[75] Inventors: Heinz Fabian, Hanau; Stephan Thomas, Grobkrotzenburg, both of Fed. Rep. of Germany

[73] Assignee: Heraeus Quarzglas GmbH, Hanau am Main, Fed. Rep. of Germany

[21] Appl. No.: 898,439

[22] Filed: Jun. 15, 1992

[30] Foreign Application Priority Data

Feb. 28, 1992 [DE] Fed. Rep. of Germany .... 4206182.2

[51] Int. Cl.$^5$ ............................................. G02B 5/172
[52] U.S. Cl. ................................................. 385/142
[58] Field of Search ............... 385/141, 142, 143, 146, 385/147

[56] References Cited

U.S. PATENT DOCUMENTS

| | | | |
|---|---|---|---|
| 4,504,114 | 3/1985 | Arrington | 385/142 |
| 4,915,474 | 4/1990 | Klein et al. | 350/96 |
| 4,988,162 | 1/1991 | Hayami | 385/142 X |

FOREIGN PATENT DOCUMENTS

| | | |
|---|---|---|
| 0094236 | 11/1983 | European Pat. Off. . |
| 0326847 | 8/1989 | European Pat. Off. . |
| 0401845 | 12/1990 | European Pat. Off. . |
| 0483477 | 5/1992 | European Pat. Off. . |
| 0483752 | 5/1992 | European Pat. Off. . |

OTHER PUBLICATIONS

Hitzler et al., "KrF-Laser Irradiation Induced Defects in All Silica Optical Fibers", Journal of Non-Crystalline Solids, vol. 149, pp. 107-114 (Oct. 11, 1992).

Thomon et al., "Correlation of the 5.0 and 7.6 ev Absorption Bands in $SiO_2$ with Oxygen Vacancy" Physical Review B, vol. 39, No. 2 (1989).

Taylor et al., "Dependence of the Damage and Transmission Properties of Fused Silica Fibers on the Excess Laser Wavelength" Applied Optics, vol. 27, No. 15 (1988).

Whitehurst et al., "Ultraviolet Pulse Transmission in Optical Fibres", Journal of Modern Optics, vol. 35, No. 3, 371-385 (1988).

Nishikawa et al., "Defects and Stress Phenomena in Optical Fibers," Proc. OFC, 1989, Paper THI1.

*Primary Examiner*—Akm E. Ullah
*Attorney, Agent, or Firm*—Felfe & Lynch

[57] ABSTRACT

A component for the transmission of light of high energy density with a wavelength between 250 nm and 400 nm is made of synthetic, high-purity fused vitreous silica having a hydroxyl ion content in the range between 50 ppm and 1200 ppm and an under-stoichiometric content of oxygen for the achievement of a minimal transmission variation in the transmission of the light.

19 Claims, 1 Drawing Sheet

COMPONENT FOR THE TRANSMISSION OF HIGH-ENERGY LIGHT, AND THE APPLICATION OF THE COMPONENT

BACKGROUND OF THE INVENTION

The invention relates to a component for the transmission of light of high energy density with a wavelength between 250 nm and 400 nm, made of synthetic, high-purity fused vitreous silica, with a light input area having a light entry surface, a light output area having a light exit surface, and a light transmission portion disposed between the light input area and the light output area, and to the use of the component.

Such components are used for the transmission of ultraviolet light of high energy density, especially for the transmission of the light of excimer lasers, for the processing of materials, or in the medical field for the treatment of vascular diseases, or in ophthalmology. The use of such components for the transmission of laser radiation int he ultraviolet spectral range is limited, however, by what is known as "photodegradation." This refers to the reduction of transmission due to the attenuation induced by the high-energy radiation. This effect of "photodegradation," which is all the more pronounced the greater the energy density of the light to be transmitted is, has been observed also at the excimer laser wavelengths of 351 nm (Xf), 308 nm (XeCl) and 248 nm (KrF). In addition to plainly visible macroscopic defects, such as fusion of the surface, spalling or cracking, the reduction of transmission can be caused by microscopic faults in the glass structure.

In the paper written by Rod S. Taylor et al., "Dependence of the damage and transmission properties of fused silica fibers on the excimer laser wavelength," published in Applied Optics, Vol. 27, No. 15 (1988), the radiation resistance of components is studied in regard to the transmission of certain excimer laser radiation in the wavelength range of 193 nm to 351 nm. The components tested are fibers of undoped, synthetic fused vitreous silica with a hydroxyl ion content between 325 ppm and 1200 ppm. It is shown that, with the exception of the 351 nm excimer laser wavelength, the transmission of the fibers diminishes with increasing time of operation, but some time after irradiation by the high-energy laser light, a partial recovery of the transmission is to be observed. Furthermore, in this article, in a direct comparison of the changes in the transmission of fused silica fibers with a hydroxyl ion content of 400 ppm in comparison with those with 1200 ppm, it was found that, at the same wavelength and the same energy of the radiation transmitted by the fibers, the fibers with a hydroxyl ion content of 400 ppm underwent the least alteration of their transmission.

An article by C. Whitehurst et al., "Ultraviolet pulse transmission in optical fibers," Journal of Modern Optics, 1988, vol. 35, No. 3, 371-385, describes components which consist of a fused vitreous silica containing up to 1500 ppm of hydroxyl ions, and having a "destruction threshold" that tends toward the higher energy densities in comparison to pure, "dry" vitreous silica. In this article is described also the formation of components from fused vitreous silica containing hydroxyl ions, having a light input section with a light entry surface, a light output section with a light exit surface, and a light transmission section disposed between the light input section and the light output section, in which the light input section is in the form of a cone tapering in the direction in which the light enters.

From the paper, "Defects and Stress Phenomena in Optical Fibers," by H. Nishikawa et al., Proc. OFC, 1989, Paper THII, measurements of the absorption of optical fibers have become known, in which the fibers are characterized by their content of oxygen ions, the method of their manufacture, their chlorine ion content and their hydroxyl ion content. On the fibers with an under-stoichiometric content of oxygen an absorption was measured at 245 nm, and this absorption band is associated with a kind of defect intrinsically present on account of the under-stoichiometric oxygen content of the glass structure, namely so-called "oxygen vacancies." Similar measurements have also been published by R. Tohmon et al. in the paper, "Correlation of the 5.0- and 7.6-eV absorption bands in $SiO_2$ with oxygen vacancy," Physical Review B, Vol. 39 (1989), No. 2. On the basis of measurements and corresponding calculations it is shown that the absorption bands at 5.0 eV (245 nm) observed in different high-purity fused silicas are to be attributed to oxygen vacancies and other oxygen-deficit defects. The fused silicas used for the measurements are also characterized by the nature of their manufacture and by their contents of chlorine ions and hydroxyl ions.

In connection with high-energy radiation in the wavelength range between 250 nm and 400 nm the known components of fused silica show a decrease of transmission from the start of the light input. Starting out from an initial value, the transmission of the components diminishes down to a "plateau" after which it changes only slightly even through fairly long operation. It has been found that these changes of the transmission from its initial level to the "plateau" definitely increase as the energy density of the radiation being transmitted increases. For a great number of applications, however, great changes in transmission during the use of the component are not tolerable. Since it is precisely the maximum transmittable energy density that is the deciding parameter for most applications, the usefulness of the known components is greatly restricted by the effect of this "photodegradation."

SUMMARY OF THE INVENTION

The present invention is addressed to the problem of specifying a component which will have the least possible transmission variation in the transmission of light of high energy density and a wavelength between 250 nm and 400 nm.

According to the invention, the fused vitreous silica has a hydroxyl ion content in the range between 50 ppm and 1200 ppm and an under-stoichiometric content of oxygen. The transmission of ultraviolet radiation necessarily produces defects in the material of the component. The nature of the defects, their concentration and their effects on transmission depend substantially on the energy density and the wavelength of the radiation being transmitted. At the same time, so-called "excess-oxygen defects" can develop, among others, which can lead to the formation or intensification of absorption bands at various wavelengths in the ultraviolet and infrared spectrum. It has been found especially that an absorption band with a maximum at 265 nm can be correlated with the formation of such "excess-oxygen defects." In addition to the characteristic of the light to be transmitted, the probability of the formation of such defects also depends on the glass structure, especially on the strength and the nature of the atomic bonds as well as the coordination of the silicon atoms or the average frequency of occurrence of oxygen ions in the vicinity of the silicon.

The under-stoichiometric oxygen content in the fused silica assures that the probability of the formation of such "excess-oxygen defects" in the transmission of high-energy radiation of a wavelength between 250 nm and 400 nm will be reduced.

On the other hand, however, even a gradual accumulation of such defects would result in a steadily worsening transmission in the component. But by means of the hydroxyl ion content in the fused silica it is possible, as known, to cure defects already developed. In the course of the transmission of high-energy light, the competing effects of the formation of defects and curing of defects form an approximate defect equilibrium in the component, which determines the "plateau" of the transmission, i.e., the decrease from the original transmission. Now it has surprisingly been found that the defects produced in "oxygen-poor," high-purity fused silica by the transmission of ultraviolet, high-energy light with a wavelength between 250 nm to 400 nm are such that the hydroxyl ions present in the fused silica network, especially the hydrogen contained therein, can bring about an especially effective curing of these defects, so that the drop in transmission from the original value to the "plateau" is very slight.

The term, "high-purity" refers herein to a fused silica whose total content of alkali ions is less than 150 ppb, whose total alkaline earth ion content is less than 100 ppb, and whose content of other metallic impurities such as titanium, chromium, iron and nickel totals less than 50 ppb.

A component has proven to be especially advantageous in which the fused silica has a hydroxyl ion content of less than 600 ppm and the under-stoichiometric oxygen content is such that the fused silica has an absorption band with a maximum in the wavelength range of 240 nm to 250 nm, with an intensity of more than 0.1 dB/m. The intensity of the absorption bands in this case means the attenuation in dB/m which corresponds to the height of the maximum of the absorption bands above the base line of the absorption bands. The fact that the under-stoichiometric oxygen content is at least great enough to produce an absorption band in the fused silica of at least 0.1 dB/m at the maximum assures that so few "excess-oxygen defects" are formed that the absorption that it produces at 265 nm is nil or hardly noticeable, and that The defects simultaneously produced in the fused silica that is low in oxygen by the high-energy radiation with wavelengths between 250 nm and 400 nm can be very effectively cured either by relatively low hydroxyl ion concentrations of 50 ppm to 600 ppm, or at least produce little or no absorption in the wavelength range around 250 nm to about 400 nm. Therefore the defects do not impede or scarcely impede the transmission of high-energy radiation in this wavelength range. Also, the relatively low hydroxyl ion content of the fused silica, of less than 600 ppm, has an advantageous effect on the transmission of the fused silica, for it has been found that high hydroxyl ion contents in fused vitreous silicas also can contribute to the formation of defects in the transmission of high-energy radiation. A hydroxyl ion content of at least 200 ppm, however, has proven to be beneficial.

Especially for the sake of an unhampered transmission of light of high energy density over a wide range of wavelengths, it has proven advantageous for the component to contain fused vitreous silica which has but a single absorption band in the wavelength range between 200 nm and 350 nm.

For the transmission of high-energy light over a relatively long distance it has been found advantageous to make the light transmission section in the form of a fiber or in the form of a rod. At the same time it is especially desirable to make the light input section and/or the light output section in the form of a cone tapering toward the light transmission section. Since the destruction threshold of the surface of a component is lower than that of the solid material, damage or destruction of the input surface or output surface can occur in the case of the input or even in the output of radiation, even at power densities which could be handled by the solid material of the component. By making these input and output surfaces greater than the cross section of the actual light transmission section, and thereby creating the possibility of a broadening of the light beam to be put in or put out, the optical load per unit area of the surface is reduced. This permits the transmission of high-energy radiation which otherwise would destroy the surfaces of the component upon entering or leaving it on account of their high optical power densities.

To compensate for the special radiation characteristics of the light to be coupled in or out, it has also proven to be advantageous to make the light entry surface and/or the light exit surface curved.

Especially for carrying high-energy radiation over relatively long distances or through curves it has proven to be advantageous to encase at least the light-transmitting part of the component in a jacket of material whose refractive index is lower than 1.4589. Fused vitreous silica doped with fluorine and/or boron, or plastic resistant to ultraviolet rays, have proven to be good jacketing materials.

The use of the component according to the invention has proven especially advantageous for the transmission of high-energy light in the wavelength range between 300 nm and 320 nm, especially with a wavelength around 310 nm. The defects produced by the radiation in this wavelength range are either cured very easily in the component according to the invention, or they produce only those absorption bands which do not interfere with the transmission of light in this wavelength range.

In an embodiment in which the light transmission section is in the form of a fiber or in the form of a rod, the component according to the invention has proven valuable for use as a single element in a flexible arrangement of several identical or geometrically similar individual elements with their longitudinal axes running parallel or substantially parallel to one another for the transmission of ultraviolet light of high energy densities for the treatment of materials. In this case the components can be embedded in a hardenable material and/or twisted together, for example.

For special applications a component has proven advantageous in which the light transmission section is in the form of a thick-walled hollow cylinder or in the form of a perforated disk. This embodiment especially suitable as a beam expander in the transmission of ultraviolet light and/or for the homogenizing of the light energies issuing from individual light rays of a beam in a plane perpendicular to the direction of light propagation. It has been found that high-energy radiation from the wavelength range between 250 nm and 400 nm, which issues for example from individual light wave conductors assembled in a bundle, can advantageously be coupled into such a component, while the light modes issuing from the individual light wave conductors mix together in the course of their transmission through the length of the light transmission section. For this purpose the length of the light transmission section is advantageously selected so that on the end of the component remote from the light wave conductor bundle, the light energies of the individual light rays at least partially overlap on account of their divergence. A material or tissue to be treated or removed can thus be irradiated uniformly with high energy over a larger surface area. The channel in the hollow cylinder can in that case serve to carry gaseous or liquid media as well as for the passage of guide wires. This is important in the case, for example, of the ablative treatment of deposits in blood vessels by means of a medical catheter which is composed of individual fibers running with their longitudinal axes parallel to one another, through which the working light is transmitted.

DETAILED DESCRIPTION OF THE PREFERRED EMBODIMENT

Figure 1:
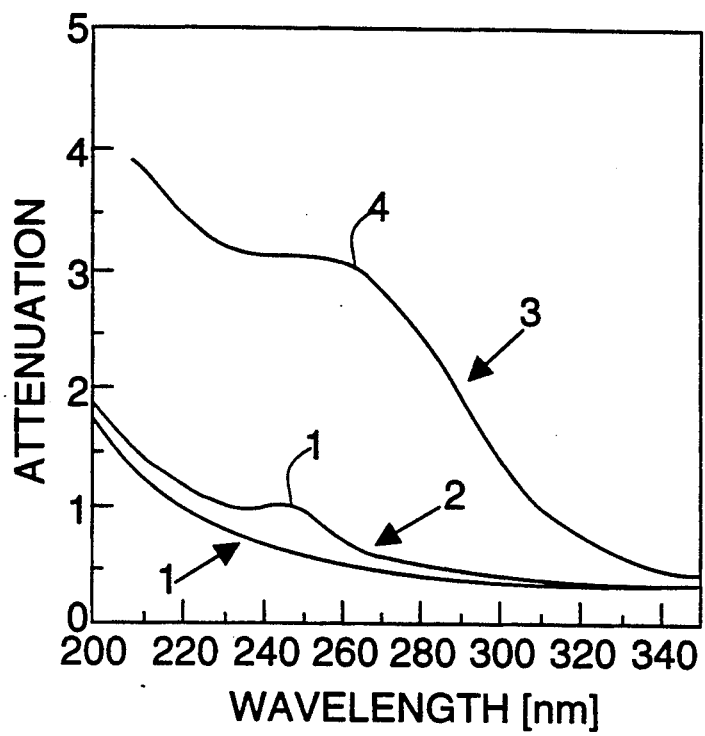
FIG. 1 shows a measurement of the attenuation of various light wave conductors, and FIG. 2 a measurement of the photodegradation in the transmission of light of high energy density with a high pulse, frequency of a component according to the invention 2a, in comparison to the photodegradation 1a of a component according to the state of the art.

The curves 1, 2 and 3 shown in FIG. 1 represent the attenuation of light wave conductors which have been made in each case by the same process from undoped, high-purity, synthetic quartz. The material of the light wave conductors differs only according to the different oxygen supply during the production of the material. Light wave conductors 1, 2 and 3 were drawn from preforms whose hydroxyl ion content amounted in each case to 600 ppm.

The fused vitreous silica for light-wave conductor 1 was produced with an oxygen supply corresponding to the amount necessary for producing a fused vitreous silica with the correct material stoichiometry (silicon : oxygen = 1 : 2). In the production of the material for light-wave conductor 2 the oxygen supply was considerably reduced, while in the production of the fused silica for light-wave conductor 3 an excess oxygen supply was chosen.

By means of a plasma external coating process, fluorine-doped fused silica jacket layers were applied to the fused silica glass cylinders thus prepared, the ratio between the outside diameter of the jacket and the core diameter amounting to 1.1. From the preforms thus produced, the light-wave conductors 1, 2 and 3 were drawn with a fiber diameter of 220 $\mu$m.

The basic attenuation curves of the light-wave conductors 1, 2 and 3 in the spectral range between 200 nm and 350 nm show significant differences, which are to be attributed only to the different oxygen supply used in the production of the fused silica. The light-wave conductor 1 shows a curve which is determined by the increase in the scattering toward shorter wavelengths. Light-wave conductor 3, whose core consists of a fused silica with an over-stoichiometric oxygen content, has a broad absorption band 4 with a maximum at about 265 nm, which determines the characteristic curve in the tested spectral range. This absorption band 4 can lead to the conclusion that so-called "excess oxygen defects" are present.

The basic attenuation of light-wave conductor 2, whose core consists of a fused silica with an under-stoichiometric oxygen content, however, shows a relatively weak narrow-band absorption 5 with a maximum at about 245 nm. This band 5, whose intensity amounts to about 0.2 dB/m, indicates the presence of so-called "oxygen vacancies" or other oxygen defects.

Figure 2:
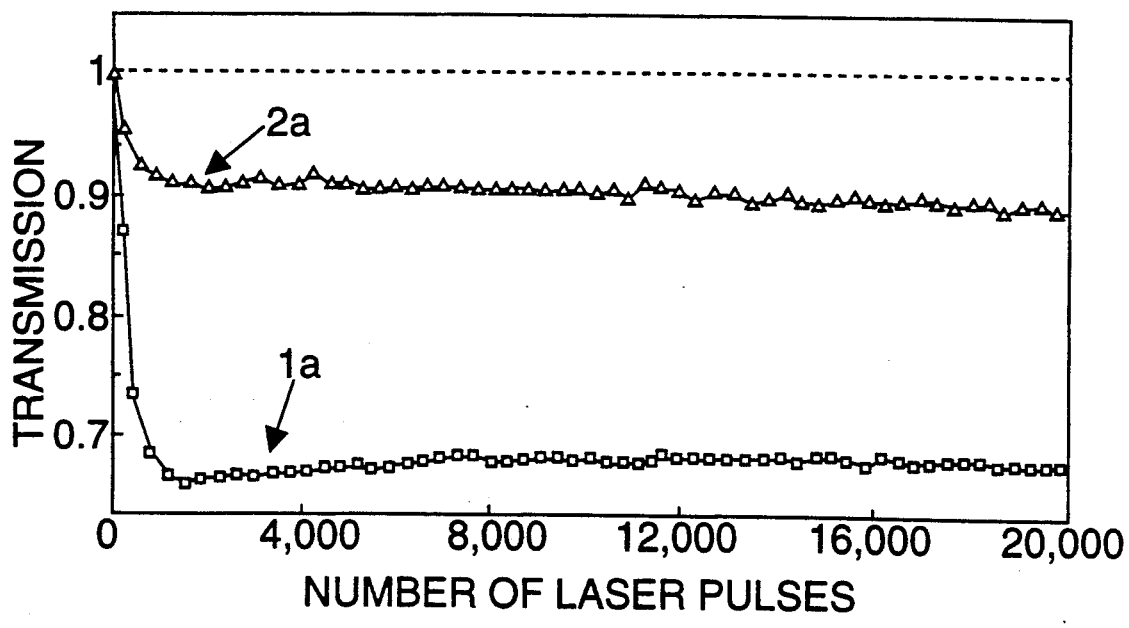

Then, high-energy XeCl excimer laser light was transmitted through portions of light-wave conductors 1 and 2 and the photodegradation was measured. The wavelength of the excimer laser light amounted to 308 nm, the pulse duration 28 ns, the energy density 15 J/cm$^2$ and the pulse frequency 30 Hz. The light-wave conductors 1a and 2a (FIG. 2) were test samples about 2 meters long. The results of these measurements are represented in FIG. 2, and they show the strong influence of the oxygen supply during the production of the core material on the photodegradation properties of the light-wave conductors made from it.

The light-wave conductor marked with the reference number 1a, which corresponds to the state of the art stoichiometric oxygen content, shows a rapid drop of the original transmission to a "plateau," and after about 20,000 laser pulses, a transmission of approximately 70% in comparison with the level at the start of the radiation. The light-wave conductor 2a, whose core consists of low-oxygen fused vitreous silica, shows a better photodegradation behavior. After 20,000 laser pulses the transmission in this light-wave conductor 2a is still better than 90% of its original level. Even after 100,000 laser pulses, the transmission of light-wave conductor 2a was still 90% of the original level.

We claim:

1. Component for the transmission of light of high energy density with a wavelength between 250 nm and 400 nm, made of synthetic, high-purity fused vitreous silica, with a light input section having a light entry surface, a light output section having a light exit surface, and a light transmission section disposed between the light input section and the light output section, wherein the fused silica has a hydroxyl ion content in the range between 50 ppm and 1200 ppm and an under-stoichiometric content of oxygen.

2. Component according to claim 1 wherein the fused vitreous silica has a hydroxyl ion content of less than 600 ppm, and the under-stoichiometric content of oxygen is such that the fused silica has an absorption band with a maximum in the wavelength range of 240 nm to 250 nm with an intensity of more than 0.1 dB/m.

3. Component according to claim 1 wherein the fused vitreous silica has a hydroxyl ion content of at least 200 ppm.

4. Component according to claim 1 wherein the fused vitreous silica has only a single absorption band in the wavelength range between 200 nm and 350 nm.

5. Component according to claim 1 wherein the light transmission section is in the form of a rod.

6. Component according to claim 5 wherein the light input section and/or the light output section is in the form of a cone tapering toward the light transmission section.

7. Component according to claim 1 wherein at least one of the light input surface and the light output surface is curved.

8. Component according to claim 1 wherein at least the light transmission section is enveloped by a jacket material which has an index of refraction of less than 1.4589.

9. Component according to claim 8 wherein the jacket material contains fused vitreous silica doped with at lest one of fluorine and boron.

10. Component according to claim 8 wherein the jacket material contains a plastic resistant to ultraviolet rays.

11. Component according to claim 1 wherein the light transmission section is in the form of a thick-walled hollow cylinder.

12. Component according to claim 1 wherein the light transmission section is in the form of a perforated disc.

13. Component according to claim 1 wherein the light transmission section is in the form of a fiber.

14. A plurality of components as claimed in claim 13 wherein said components have longitudinal axes running in parallel and are arranged in a bundle.

15. Component according to claim 1 wherein the under-stoichiometric content of oxygen is such that the fused silica has an absorption band with a maximum in the wavelength range of 240 nm to 250 nm with an intensity of more than 0.1 dB/m.

16. Method for transmitting light of high energy density with a wavelength between 300 nm and 320 nm comprising providing a component made of synthetic high purity fused vitreous silica, with a light input section having a light entry surface, a light output section having a light exit surface, and a light transmission section disposed between the light input section and the light output section, wherein the fused silica has a hydroxyl ion content in the range between 50 ppm and 1200 ppm and an under-stoichiometric content of oxygen, and transmitting said light through said component.

17. Method for expanding a beam of light in a plane perpendicular to the direction of propagation of said beam, comprising providing a component made of synthetic high purity fused vitreous silica, with a light input section having a light entry surface, a light output section having a light exit surface, and a light transmission section in the form of a thick walled hollow cylinder disposed between the light input section and the light output section, wherein the fused silica has a hydroxyl ion content in the range between 50 ppm and 1200 ppm and an under-stoichiometric content of oxygen, and directing said beam into said light input section.

18. Method according to claim 16 wherein the under-stoichiometric content of oxygen is such that the fused silica has an absorption band with a maximum in the wavelength range of 240 nm to 250 nm with an intensity of more than 0.1 dB/m.

19. Method according to claim 17 wherein the under-stoichiometric content of oxygen is such that the fused silica has an absorption band with a maximum in the wavelength range of 240 nm to 250 nm with an intensity of more than 0.1 dB/m.

* * * * *